(12) United States Patent
Kinney et al.

(10) Patent No.: US 7,087,813 B2
(45) Date of Patent: Aug. 8, 2006

(54) PLANT LIPOXYGENASES

(75) Inventors: Anthony J. Kinney, Wilmington, DE (US); Theodore M. Klein, Wilmington, DE (US); Jian-Ming Lee, West Caldwell, NJ (US); Richard W. Pearlstein, Newark, DE (US); J. Antoni Rafalski, Wilmington, DE (US); Jennie Bih-Jien Shen, Wilmington, DE (US); Catherine J. Thorpe, Cambridge (GB); Scott V. Tingey, Wilmington, DE (US)

(73) Assignee: E.I. du Pont de nemours and Company, Wilmington, DE (US)

( * ) Notice: Subject to any disclaimer, the term of this patent is extended or adjusted under 35 U.S.C. 154(b) by 142 days.

(21) Appl. No.: 10/059,909

(22) Filed: Jan. 29, 2002

(65) Prior Publication Data

US 2003/0074693 A1 Apr. 17, 2003

Related U.S. Application Data

(63) Continuation-in-part of application No. 09/501,422, filed on Feb. 9, 2000, now abandoned.

(60) Provisional application No. 60/119,597, filed on Feb. 10, 1999.

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .......................... 800/295; 435/6; 435/69.1; 435/468; 435/419; 435/252.3; 435/320.1; 435/183; 530/370; 536/23.6; 800/278

(58) Field of Classification Search ................ 435/6, 435/69.1, 468, 419, 252.3, 320.1; 530/370; 536/23.6; 800/278, 295
See application file for complete search history.

(56) References Cited

PUBLICATIONS

Sabine Rosahl, Z. Naturforsch, vol. 51:123–138, 1996, Lipoxygenases in Plants—Their Role in Development and Stress Response.
Kirsten Voros et al., Eur. J. Biochem., vol. 251:36–44, 1998, Characterization of a Methljasmonate–Inducible Lipoxygenase from Barley (*Hordeum vulgare* CV. Salome) Leaves.
Joaquin Royo et al., Journ. of Biol. Chem., vol. 271(35):21012–21019, 1996, Characterization of Three Potato Lipoxygenases with Distinct Enzymatic Activities and Different Organ–Specific and Wound–Regulated Expression Patterns.
You–Liang Peng et al., Journ. of Biol. Chem., vol. 269(5):3755–3761, 1994, A Novel Lipoxygenase from Rice.
National Center for Biotechnology Information General Identifier No. 1495802, Sep. 27, 1996, J. Royo et al., Characterization of Three Potato Lipoxygenases with Distinct Enzymatic Activities and Different Organ–Specific and Wound–Regulated Expression Patterns.
National Center for Biotechnology Information General Identifier No. 765203, Apr. 12, 1995, A. Geerts et al., Expression of Lipoxygenase in Wounded Tubers of Solanium Tuberosum L.
John A. Sandoval et al., Plant Phys., vol. 109:269–275, 1995, N–Acylphosphatidylethanolamine in Dry and Imbibing Cottonseeds.
National Center for Biotechnology Information General Identifier No. 2182267, Jul. 6, 1999, J. R. Van Mechelen et al., Molecular Characterization of Two Lipoxygenases from Barley.
National Center for Biotechnology Information General Identifier No. 3668063, Sep. 29, 1998, K. Matsui et al., Nucleotide Sequence of a Cucumber Cotyledon Lipoxygenase CDNA.
Kenji Matsui et al., Plant Phys., vol. 109:337–339, 1995, Plant Gene Register PGR95–044, Nucleotide Sequence of a Cucumber Cotyledon Lipoxygenase CDNA.
National Center for Biotechnology Information General Identifier No. 126401, Feb. 1, 1995, H. Ohta et al., CDNA Cloning of Rice Lipoxygenase L–2 and Characterization Using an Active Enzyme Expressed from the CDNA in *Escherichia coli*.
Hiroyuki Ohta et al., Eur. J. Biochem., vol. 206;331–336, 1992, CDNA Cloning of Rice Lipoxygenase L–2 and Characterization Using an Active Enzyme Expressed from the CDNA in *Escherichia coli*.
Jan R. Van Mechelen et al., Plant Mol. Biol, vol. 39:1283–1298, 1999, Molecular Characterization of Two Lipoxygenases from Barley.
Eliane Lazar et al., Mol & Cell. Biol, vol. 8(3):1247–1252, 1988, Transforming Growth Factor Alpha:Mutation of Aspartic Acid 47 and Leucine 48 Results in Different Bilogical Activities.
Wilson H. Burgess et al., J. of Cell Biol, vol. 111:2129–2138, 1990, Possible Dissocation of The Heparin– Binding and Mitogenic Activities of Heparin–Binding (Acidic Fibroblast) Growth Factor–1 from its Receptor–Binding Activities by Site–Directed Mutagenesis of a Single Lysine Residue.
Pierre Broun et al., Science, vol. 282:131–133, 1998, Catalytic Plasticity of Fatty Acid Modification Enzymes Underlying Chemical Diversity of Plant Lipids.

(Continued)

*Primary Examiner*—Phuong T. Bui
(74) *Attorney, Agent, or Firm*—Cozen O'Connor, P.C.; Lori Y. Beardell, Esq.; Gwilym J. O. Attwell, Esq.

(57) ABSTRACT

This invention relates to isolated nucleic acid fragments encoding lipoxygenases. The invention also relates to the construction of recombinant DNA constructs encoding all or a portion of the lipoxygenase, in sense or antisense orientation, wherein expression of the recombinant DNA construct results in production of altered levels of the lipoxygenase in a transformed host cell.

11 Claims, No Drawings

OTHER PUBLICATIONS

Peer Bork, Gen. Res., vol. 10:398–410, 2000, Powers and Pitfalls in Sequence Analysis: The 70% Hurdle.

Michaela Hohne et al., Eur J. Biochem., vol. 241:6–11, 1996, Lipid Body Lipoxygenase Characterized by Protein Fragmentation, CDNA Sequence and Very Early Expression of The Enzyme During Germination of Cucumber Seeds.

US 7,087,813 B2

PLANT LIPOXYGENASES

This application is a continuation-in-part of U.S. application No. 09/501,422, filed Feb. 09, 2000, now abandoned, which claims the benefit of U.S. Provisional Application No. 60/119,597, filed Feb. 10, 1999.

FIELD OF THE INVENTION

This invention is in the field of plant molecular biology. More specifically, this invention pertains to nucleic acid fragments encoding lipoxygenases in plants and seeds.

BACKGROUND OF THE INVENTION

Lipoxygenases are membrane-bound ubiquitous enzymes which catalyze the hydroperoxidation of polyunsaturated fatty acids in the first step of fatty acid metabolite synthesis. Products of this pathway are found as signal molecules, involved in growth and development regulation, in senescence, and in response to pathogen invasion and wound stress (Rosahl (1996) *Z. Naturforsch.* [C] 51:123–138). Lipoxygenases with different specificities, subcellular location, and tissue-specific expression patterns have been identified in several plants including rice, barley, soybean, tomato, cucumber and potato.

Many lipoxygenase cDNAs have been identified in barley, but two isozymes have been characterized, lipoxygenase 1 and 2. The amino acid sequence of proteolytic fragments from the barley isozyme 1 are identical to the predicted partial amino acid sequences from the potato IoxA and the rice L2. The methyljasmonate-induced 100 kDa lipoxygenase has been characterized as a barley isozyme 2 (Voros et al. (1998) *Eur. J. Biochem.* 25:36–44). As a response to wounding, the potato Lox1 is expressed mainly in tubers and roots while Lox2 is expressed almost exclusively in leaves and Lox3 in leaves and roots. Linoleic acid is preferentially utilized as a substrate by Lox1 which produces mainly 9-hydroperoxides. Utilizing the same substrate, the major product of Lox2 and Lox3 is the jasmonic acid precursor 13-hydroperoxilinolenic acid (Royo et al. (1996) *J. Biol. Chem.* 271:1012–1019). Fungal infection of plants has allowed the identification of lipoxygenases which are induced upon microbial treatment such as the rice lipoxygenase L2 which introduces a molecular oxygen into the C-13 position of linoleic and linolenic acid (Peng et al. (1994) *J. Biol. Chem.* 269:3755–3761).

Because lipoxygenases play so many different roles and have different specificities, knowing the amino acid sequences for lipoxygenases present in different plants will allow the understanding of plant development and wound response.

SUMMARY OF THE INVENTION

The present invention concerns isolated polynucleotides comprising a nucleotide sequence encoding a polypeptide having lipoxygenase activity wherein the amino acid sequence of the polypeptide and the amino acid sequence of SEQ ID NO:2, 4, 6, 8, 10, 12, 14, 16, or 18 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence, wherein the complement and the nucleotide sequence contain the same number of nucleotides and are 100% complementary. More specifically, the present invention concerns isolated polynucleotides encoding the polypeptide sequence of SEQ ID NO:2, 4, 6, 8, 10, 12, 14, 16, or 18 or nucleotide sequences comprising the nucleotide sequence of SEQ ID NO:1, 3, 5, 7, 9, 11, 13, 15, or 17.

In a first embodiment, the present invention concerns an isolated polynucleotide comprising: (a) a nucleotide sequence encoding a polypeptide comprising at least 100 amino acids, wherein the amino acid sequence of the polypeptide and the amino acid sequence of SEQ ID NO:2, 4, 6, 8, 10, 12, 14, 16, or 18 have at least 80%, 85%, 90%, or 95% identity based on the Clustal alignment method, or (b) the complement of the nucleotide sequence, wherein the complement and the nucleotide sequence contain the same number of nucleotides and are 100% complementary. The polypeptide preferably comprises the amino acid sequence of SEQ ID NO:2, 4, 6, 8, 10, 12, 14, 16, or 18. The nucleotide sequence preferably comprises the nucleotide sequence of SEQ ID NO:1, 3, 5, 7, 9, 11, 13, 15, or 17. The polypeptide preferably is a lipoxygenase.

In a second embodiment, the present invention relates to a recombinant DNA construct comprising any of the isolated polynucleotides of the present invention operably linked to a regulatory sequence, and a cell, a plant, and a seed comprising the recombinant DNA construct.

In a third embodiment, the present invention concerns a vector comprising any of the isolated polynucleotides of the present invention.

In a fourth embodiment, the present invention relates to an isolated polynucleotide comprising a nucleotide sequence comprised by any of the polynucleotides of the first embodiment, wherein the nucleotide sequence contains at least 30, 40, or 60 nucleotides.

In a fifth embodiment, the present invention concerns a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell. The invention also concerns the transgenic plant produced by this method, and the seed obtained from this transgenic plant.

In a seventh embodiment, the present invention concerns an isolated polypeptide comprising an amino acid sequence comprising at least 100 amino acids, wherein the amino acid sequence and the amino acid sequence of SEQ ID NO:2, 4, 6, 8, 10, 12, 14, 16, or 18 have at least 80%, 85%, 90%, or 95% identity based on the Clustal alignment method. The amino acid sequence preferably comprises the amino acid sequence of SEQ ID NO:2, 4, 6, 8, 10, 12, 14, 16, or 18. The polypeptide preferably is a lipoxygenase.

In an eight embodiment, the invention relates to a method for isolating a polypeptide encoded by the polynucleotide of the present invention comprising isolating the polypeptide from a cell containing a recombinant DNA construct comprising the polynucleotide operably linked to a regulatory sequence.

In a ninth embodiment, the present invention concerns a virus, preferably a baculovirus, comprising any of the isolated polynucleotides of the present invention or any of the recombinant DNA constructs of the present invention.

In a tenth embodiment, the invention relates to a method of selecting an isolated polynucleotide that affects the level of expression or activity of a gene encoding a lipoxygenase protein in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of expression or activity of the lipoxygenase in the host cell containing the isolated polynucleotide; and (d) comparing the level of expression or activity of the lipoxygenase in the host cell containing the isolated polynucleotide with the level of expression or activity of the lipoxygenase in the host cell that does not contain the isolated polynucleotide.

In an eleventh embodiment, the invention concerns a method of obtaining a nucleic acid fragment encoding a substantial portion of a lipoxygenase protein, preferably a plant lipoxygenase protein comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs: 1, 3, 5, 7, 9, 11, 13, 15, or 17, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a lipoxygenase protein amino acid sequence.

In a twelfth embodiment, this invention relates to a method of obtaining a nucleic acid fragment encoding all or a substantial portion of the amino acid sequence encoding a lipoxygenase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a fourteenth embodiment, this invention relates to a method of altering the level of expression or activity of a lipoxygenase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the lipoxygenase protein in the transformed host cell.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Lipoxygenase Isozymes

| Protein | Clone Designation | SEQ ID NO: (Nucleotide) | SEQ ID NO: (Amino Acid) |
|---|---|---|---|
| Balsam Pear Lipoxygenase Isozyme | fds.pk0001.b6 | 1 | 2 |
| Garden Balsam Lipoxygenase Isozyme | ids.pk0019.d2 | 3 | 4 |
| Corn Lipoxygenase Isozyme | Contig of: csc1c.pk001.d6 p0126.cnlau43r | 5 | 6 |
| Corn Lipoxygenase Isozyme | p0118.chsbc64r | 7 | 8 |
| Corn Lipoxygenase Isozyme | p0128.cpicn02r | 9 | 10 |
| Balsam Pear Lipoxygenase Isozyme | fds.pk0001.b6:fis | 11 | 12 |
| Garden Balsam Lipoxygenase Isozyme | ids.pk0019.d2:fis | 13 | 14 |
| Corn Lipoxygenase Isozyme | p0118.chsbc64r:fis | 15 | 16 |
| Corn Lipoxygenase Isozyme | p0126.cnlau43r:fis | 17 | 18 |
| Lipoxygenase Domain I | | | 19 |
| Lipoxygenase Domain II | | | 20 |
| Lipoxygenase Domain III | | | 21 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, 3, 5, 7, 9, 11, 13, 15, or 17, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to a regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from SEQ ID NO:1, 3, 5, 7, 9, 11, 13, 15, or 17 and the complement of such nucleotide sequences may be used to affect the expression, activity, and/or function of a lipoxygenase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of lipoxygenase polypeptide or enzyme activity in the host cell containing the isolated polynucleotide or recombinant DNA construct; and comparing the level of lipoxygenase polypeptide or enzyme activity in the host cell containing the isolated polynucleotide or recombinant DNA construct with the level of lipoxygenase polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys*. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol*. 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence encoding a lipoxygenase polypeptide having at least 80% identity, based on the Clustal method of alignment, when compared to a polypeptide of SEQ ID NO:2, 4, 6, 8, 10, 12, 14, 16, or 18.

This invention also relates to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several lipoxygenases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other lipoxygenases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci.* USA 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NO:1, 3, 5, 7, 9, 11, 13, 15, or 17 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol*. 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

The nucleic acid fragments of the instant invention may be used to create transgenic plants in which the disclosed polypeptides are present at higher or lower levels than normal or in cell types or developmental stages in which they are not normally found. This would have the effect of altering the level of pathogen resistance in those cells. Overexpression of lipoxygenase isozymes in transgenic plants will result in the production of novel oils containing fatty acids with double bounds. These novel oils can be used as drying agents and as livestock feed supplement to enhance lean body mass. Blocking the expression of the lipoxygenase gene in developing wheat kernels will result in improved stability of the grain. The protein and oil products from soybeans having suppressed lipoxygenases will have improved flavor. The lipoxygenase sequence may be used to obtain the lox promoter(s). This promoter(s) may be used in combination with various structural gene sequences to achieve crops with improved flavor and protein functionality.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide (or recombinant DNA construct) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) Mol. Gen. *Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the recombinant DNA construct described above may be further supplemented by directing the coding sequence to encode the instant polypeptide with appropriate intracellular targeting sequences such as transit sequences (Keegstra (1989) *Cell* 56:247–253), signal sequences, or sequences encoding endoplasmic reticulum localization (Chrispeels (1991) *Ann. Rev. Plant Phys. Plant Mol. Biol.* 42:21–53) or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a lipoxygenase polypeptide having an amino acid sequence that is at least 80% identical, based on the Clustal method of alignment, to a polypeptide of SEQ ID NO:2, 4, 6, 8, 10, 12, 14, 16, or 18.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded lipoxygenases. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402–9406; Koes et al. (1995) *Proc. Natl. Acad. Sci. USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various balsam pear, garden balsam, and corn tissues were prepared. The characteristics of the libraries are described below.

TABLE 2 cDNA Libraries from Balsam Pear, Garden Balsam, and Corn

| Library | Tissue | Clone |
| --- | --- | --- |
| csc1c | Corn 20-Day Seedling (Germination Cold Stress). The seedling appeared purple. | csc1c.pk001.d6 |
| fds | *Momordica charantia* Developing Seed | fds.pk0001.b6 |
| ids | *Impatiens balsamia* Developing Seed | ids.pk0019.d2 |
| p0118 | Corn Stem Tissue Pooled From the 4th and 5th Internodes Subtending The Tassel At Stages V8–V12*, Night Harvested** | p0118.chsbc64r |
| p0126 | Corn Leaf Tissue From V8–V10** Stages, Pooled, Night-Harvested | p0126.cnlau43r |
| p0128 | Corn Primary and Secondary Immature Ear | p0128.cpicn02r |

*Corn developmental stages are explained in the publication "How a corn plant develops" from the Iowa State University Coop. Ext. Service Special Report No. 48 reprinted June 1993.
**This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res*. 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res*. 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding lipoxygenases were identified by conducting BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Lipoxygenase Isozymes

The BLASTX search using the EST sequences from clones listed in Table 3 revealed similarity of the polypeptides encoded by the cDNAs to lipoxygenase isozymes from *Solanum tuberosum* (NCBI General Identifier Nos. 1495802 and 765203), the lipoxygenase 1 from *Hordeum vulgare* or *Cucumis sativus* (NCBI General Identifier Nos. 2182267 and 3668063, respectively), or lipoxygenase L2 from *Oryza sativa* (NCBI General Identifier No. 126401). Shown in Table 3 are the BLAST results for individual ESTs ("EST"), or for the sequences of contigs assembled from two or more ESTs ("Contig"):

TABLE 3

BLAST Results for Sequences Encoding Polypeptides Homologous to Lypoxygenase Isozymes

| Clone | Status | NCBI General Identifier No. | BLAST pLog Score |
|---|---|---|---|
| fds.pk0001.b6 | EST | 3668063 | 82.5 |
| ids.pk0019.d2 | EST | 765203 | 43.1 |
| Contig of: | Contig | 1495802 | 57.2 |
| csc1c.pk001.d6 | | | |
| p0126.cnlau43r | | | |
| p0118.chsbc64r | EST | 2182267 | 25.4 |
| p0128.cpicn02r | EST | 126401 | 74.1 |

The sequence of the entire cDNA insert in clones fds.pk0001.b6, ids.pk0019.d2, p0118.chsbc64r, and p0128.cpicn02r was determined. The BLASTP search using the amino acid sequences from clones listed in Table 4 revealed similarity of the polypeptides encoded by the cDNAs to lipoxygenase isozymes from *Solanum tuberosum* (NCBI General Identifier Nos. 1495802 and 765203), lipoxygenase 1 from *Cucumis sativus* (NCBI General Identifier No. 3668063), or lipoxygenase from *Hordeum vulgare* (NCBI General Identifier No. Accession No. 2182267). Shown in Table 4 are the BLASTP results for the sequences of the entire cDNA inserts comprising the indicated cDNA clones ("FIS"), or for FISs encoding the entire protein ("CGS"):

TABLE 4

BLAST Results for Sequences Encoding Polypeptides
Homologous to Lipoxygenase Isozymes

| Clone | Status | NCBI General Identifier No. | BLAST pLog Score |
|---|---|---|---|
| fds.pk0001.b6:fis | CGS | 3668063 | >254.00 |
| ids.pk0019.d2:fis | FIS | 765203 | >254.00 |
| p0118.chsbc64r:fis | CGS | 2182267 | >180.00 |
| p0126.cnlau43r:fis | FIS | 1495802 | 147.00 |

The nucleotide sequence of the entire cDNA insert in clone fds.pk0001.b6:fis is shown in SEQ ID NO:11. The amino acid sequence deduced from nucleotides 12 through 2651 of SEQ ID NO:11 is shown in SEQ ID NO:12. The nucleotide sequence of the entire cDNA insert in clone ids.pk0019.d2:fis is shown in SEQ ID NO:13. The amino acid sequence deduced from nucleotides 20 through 1336 of SEQ ID NO:13 is shown in SEQ ID NO:14. The nucleotide sequence of the entire cDNA insert in clone p0118.chsbc64r:fis is shown in SEQ ID NO:15. The amino acid sequence deduced from nucleotides 235 through 2895 of SEQ ID NO:15 is shown in SEQ ID NO:16. The nucleotide sequence of the entire cDNA insert in clone p0126.cnlau43r:fis is shown in SEQ ID NO:17. The amino acid sequence deduced from amino acids 96 through 1495 of SEQ ID NO:17 is shown in SEQ ID NO:18.

A number of conserved regions are known among plant Lipoxygenses. A 50 amino acid stretch (SEQ ID NO:19) towards the C-terminal half of the protein contains 5 histidines conserved in lipoxigenases. A 32 amino acid stretch (SEQ ID NO:20) includes another conserved histidine. These histidines were first identified at positions 512, 517, 522, 540, 549, and 708 of the barley LoxA (Mechelen et al. (1999) *Plant Molecular Biology* 39:1283–1298). Three of these histidines (at positions 517, 522, and 708) are considered to be necessary for iron binding and catalytic activity. The C-terminal amino acids (SEQ ID NO:21) are also conserved in lipoxygenases. The 50 amino acid domain of SEQ ID NO:19 corresponds to amino acids 532 through 581 of SEQ ID NO:12, amino acids 97 through 146 of SEQ ID NO:14, and amino acids 528 through 577 of SEQ ID NO:16. The 32 amino acid domain of SEQ ID NO:20 corresponds to amino acids 724 through 755 of SEQ ID NO:12, amino acids 289 through 320 of SEQ ID NO:14, and amino acids 720 through 751 of SEQ ID NO:16. The 8 amino acid domain of SEQ ID NO:21 corresponds to amino acids 873 through 880 of SEQ ID NO:12, and amino acids 880 through 887 of SEQ ID NO:16. In SEQ ID NO:14, the domain of SEQ ID NO:21 is found at amino acids 438 through 445, but there is a conserved change (Ile to Val) at position 443 and a non-conserved change (Pro to Ser) at position 440 of SEQ ID NO:14.

The data in Table 5 presents the percent identity of the amino acid sequences set forth in SEQ ID NOs: 2, 4 6, 8, 10,12, 14, 16, and 18 with the *Cucumis sativus*, *Solanum tuberosum*, and *Hordeum vulgare* sequences (NCBI General Identifiers Nos. 3668063, 765203, 1495802, and 2182267).

TABLE 5

Percent Identity of Amino Acid Sequences Deduced From the Nucleotide
Sequences of cDNA Clones Encoding Polypeptides
Homologous to Lipoxygenase Isozymes

| | | Percent Identity to | | | |
|---|---|---|---|---|---|
| | SEQ ID NO. | 3668063 | 765203 | 2182267 | 1495802 |
| fds.pk0001.b6 | 2 | 75.9 | 35.9 | 31.2 | 17.1 |
| ids.pk0019.d2 | 4 | 62.7 | 69.6 | 49.0 | 36.3 |
| Contig of: | 6 | 33.3 | 32.7 | 27.2 | 57.8 |
| csc1c.pk001.d6 | | | | | |
| p0126.cnlau43r | | | | | |
| p0118.chsbc64r | 8 | 22.5 | 22.5 | 61.3 | 16.2 |
| p0128.cpicn02r | 10 | 38.9 | 42.7 | 37.4 | 16.8 |
| fds.pk0001.b6:fis | 12 | 81.7 | 64.9 | 48.9 | 38.2 |
| ids.pk0019.d2:fis | 14 | 65.6 | 72.6 | 59.3 | 47.2 |
| p0118.chsbc64r:fis | 16 | 49.4 | 56.0 | 71.1 | 33.8 |
| p0126.cnlau43r:fis | 18 | 32.1 | 33.2 | 31.0 | 53.0 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion or entire lipoxygenase isozymes from balsam pear, garden balsam, and corn. These sequences represent the first balsam pear, garden balsam, and corn sequences encoding lipoxygenase isozymes known to Applicant.

Example 4

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Ncol or Smal) can be incorporated into the oligonucleotides to provide proper orientation of the DNA fragment when inserted into the digested vector pML103 as described below. Amplification is then performed in a standard PCR. The amplified DNA is then digested with restriction enzymes Ncol and Smal and fractionated on an agarose gel. The appropriate band can be isolated from the gel and combined with a 4.9 kb Ncol-Smal fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb Sall-Ncol promoter fragment of the maize 27 kD zein gene and a 0.96 kb Smal-Sall fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Ncol (which includes the ATG translation initiation codon), Smal, Kpnl and Xbal. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHl site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

The activity of the lipoxygenase introduced into monocot cells (Example 4), dicot cells (Example 5) or microbial cells (Example 6) may be evaluated. Assays may be conducted under well known experimental conditions which permit optimal enzymatic activity of the lipoxygenase as presented by Grossman and Zakut (1979) *Methods Biochem. Anal.* 25:303–329.

What is claimed is:

1. An isolated polynucleotide comprising:
   (a) a nucleotide sequence encoding a polypeptide having lipoxygenase activity, wherein the amino acid sequence of the polypeptide and the amino acid sequence of SEQ ID NO:16 have at least 90% sequence identity based on the Clustal alignment method, or
   (b) the complement of the nucleotide sequence, wherein the complement and the nucleotide sequence contain the same number of nucleotides and are 100% complementary.

2. The polynucleotide of claim 1, wherein the amino acid sequence of th polypeptide and the amino acid sequence of SEQ ID NO:16 have at least 95% identity based on the Clustal alignment method.

3. The polynucleotide of claim 1, wherein the amino acid sequence of the polypeptide comprises the amino acid sequence of SEQ ID NO:16.

4. The polynucleotide of claim 1 wherein the nucleotide sequence comprises the nucleotide sequence of SEQ ID NO:15.

5. A vector comprising the polynucleotide of claim 1.

6. A recombinant DNA construct comprising the polynucleotide at claim 1 operably linked to a regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

UNITED STATES PATENT AND TRADEMARK OFFICE
CERTIFICATE OF CORRECTION

PATENT NO. : 7,087,813 B2 Page 1 of 1
APPLICATION NO. : 10/059909
DATED : August 8, 2006
INVENTOR(S) : J. Antoni Rafalski et al.

It is certified that error appears in the above-identified patent and that said Letters Patent is hereby corrected as shown below:

Title page of patent, item (75) Inventors section: please delete "Anthony J. Kinney, Theodore M. Klein, Jian-Ming Lee, Richard W. Pearlstein, Jennie Bih-Jien Shen, Catherine J. Thorpe" and insert --Zude Weng, Vernon Hills, IL (PR); Leslie T. Harvell, Newark, DE (US)--.

Signed and Sealed this

Sixteenth Day of January, 2007

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 565
<212> TYPE: DNA
<213> ORGANISM: Momordica charantia
<220> FEATURE:
<221> NAME/KEY: unsure
<222> LOCATION: (453)
<223> OTHER INFORMATION: n = A, C, G, or T
<221> NAME/KEY: unsure
<222> LOCATION: (469)
<223> OTHER INFORMATION: n = A, C, G, or T
<221> NAME/KEY: unsure
<222> LOCATION: (499)
<223> OTHER INFORMATION: n = A, C, G, or T
<221> NAME/KEY: unsure
<222> LOCATION: (506)
<223> OTHER INFORMATION: n = A, C, G, or T
<221> NAME/KEY: unsure
<222> LOCATION: (527)
<223> OTHER INFORMATION: n = A, C, G, or T
<221> NAME/KEY: unsure
<222> LOCATION: (529)
<223> OTHER INFORMATION: n = A, C, G, or T
<221> NAME/KEY: unsure
<222> LOCATION: (553)
<223> OTHER INFORMATION: n = A, C, G, or T
<221> NAME/KEY: unsure
<222> LOCATION: (556)
<223> OTHER INFORMATION: n = A, C, G, or T

<400> SEQUENCE: 1
gagaatgttt gggattggga agagtatcat agagggcgcc gtgaacacta ccggcgacct      60
cgccggctcc gtcatcaatg ccggcggcaa tattgtaggg cgtgtcacca atatcggcgg     120
gaagaagatc aaagggacgg tggttcttat gagaagcaat gttttggact tcaccgaatt     180
tcattcctca cttcttgacg gcgtcactga gctcttgggc ggcggaattt cattgcaact     240
tatcagtgct actcacgctt ccaacgactc gcgagggaaa gttggaaagg ggcgtttct      300 ggagaggtgg ctgacttcag ttccgccact gttcgctgga gagtctgtgt ttcaagtgaa     360
ctttgattgg gaagagaact ttgggatttc caaggagctt tcttcataaa aaatgggcac     420
accagtgagt tcttcctcaa gtctgtaact ccnggaggat ttcctggcnt tggaaggtcc     480
attttgactg caactcaang gtttancctt ctcgaagata aagaaantng cattttcttt     540
gcaaaccata aanccntcca ttcaa                                           565

<210> SEQ ID NO 2
<211> LENGTH: 170
<212> TYPE: PRT
<213> ORGANISM: Momordica charantia
<220> FEATURE:
<221> NAME/KEY: UNSURE
<222> LOCATION: (155)
<223> OTHER INFORMATION: Xaa = ANY AMINO ACID
<221> NAME/KEY: UNSURE
<222> LOCATION: (164)
<223> OTHER INFORMATION: Xaa = ANY AMINO ACID
```

```
<221> NAME/KEY: UNSURE
<222> LOCATION: (166)
<223> OTHER INFORMATION: Xaa = ANY AMINO ACID

<400> SEQUENCE: 2

Met Phe Gly Ile Gly Lys Ser Ile Ile Glu Gly Ala Val Asn Thr Thr
 1               5                  10                  15

Gly Asp Leu Ala Gly Ser Val Ile Asn Ala Gly Gly Asn Ile Val Gly
                20                  25                  30

Arg Val Thr Asn Ile Gly Gly Lys Lys Ile Lys Gly Thr Val Val Leu
            35                  40                  45

Met Arg Ser Asn Val Leu Asp Phe Thr Glu Phe His Ser Ser Leu Leu
 50                  55                  60

Asp Gly Val Thr Glu Leu Leu Gly Gly Ile Ser Leu Gln Leu Ile
 65                  70                  75                  80

Ser Ala Thr His Ala Ser Asn Asp Ser Arg Gly Lys Val Gly Lys Gly
                85                  90                  95

Ala Phe Leu Glu Arg Trp Leu Thr Ser Val Pro Pro Leu Phe Ala Gly
                100                 105                 110

Glu Ser Val Phe Gln Val Asn Phe Leu Gly Arg Glu Leu Trp Asp Phe
            115                 120                 125

Gln Gly Ala Phe Phe Ile Lys Asn Gly His Thr Ser Glu Phe Phe Leu
130                 135                 140

Lys Ser Val Thr Pro Gly Gly Phe Pro Gly Xaa Lys Val His Phe Asp
145                 150                 155                 160

Cys Asn Ser Xaa Val Xaa Pro Ser Arg Arg
                165                 170

<210> SEQ ID NO 3
<211> LENGTH: 639
<212> TYPE: DNA
<213> ORGANISM: Impatiens balsamia
<220> FEATURE:
<221> NAME/KEY: unsure
<222> LOCATION: (488)..(489)
<223> OTHER INFORMATION: n = A, C, G, or T
<221> NAME/KEY: unsure
<222> LOCATION: (494)
<223> OTHER INFORMATION: n = A, C, G, or T
<221> NAME/KEY: unsure
<222> LOCATION: (526)
<223> OTHER INFORMATION: n = A, C, G, or T
<221> NAME/KEY: unsure
<222> LOCATION: (530)
<223> OTHER INFORMATION: n = A, C, G, or T
<221> NAME/KEY: unsure
<222> LOCATION: (537)
<223> OTHER INFORMATION: n = A, C, G, or T
<221> NAME/KEY: unsure
<222> LOCATION: (549)
<223> OTHER INFORMATION: n = A, C, G, or T
<221> NAME/KEY: unsure
<222> LOCATION: (572)
<223> OTHER INFORMATION: n = A, C, G, or T
<221> NAME/KEY: unsure
<222> LOCATION: (610)
<223> OTHER INFORMATION: n = A, C, G, or T
<221> NAME/KEY: unsure
<222> LOCATION: (617)
<223> OTHER INFORMATION: n = A, C, G, or T
<221> NAME/KEY: unsure
<222> LOCATION: (631)
<223> OTHER INFORMATION: n = A, C, G, or T

<400> SEQUENCE: 3
gttgaagagg caatgaatca aaacaagatt ttcatattag atcaccatga tagtttgatg    60
```

-continued

```
ccatacttgg ggagaatcaa cacaaccacc acaaagactt atgcttcaag gactcttctt    120
atccttagga aagatgggac tttgatgcca ttagccattg agctaagcct gcccaaccca    180
agaggagatg aatatggtgc catatgcaaa gtctacaccc cggctcaaca tggtgtagaa    240
gcctcccttt ggcagcttgc ttaagcctat gtcgtggtta acgactcttg tatccacgaa    300
tccgtccagt cattgggttt gaacacgcaa gcagtgattg agcatttgta atcgcgacaa    360
acagacactt agcgtacttt atccgatcaa aagttgttca ccctcatttt ccgagacacg    420
attaacatta tgcatcgcaa ggaagtacta atcacgcggg ttgagttatt gagaaacttt    480
tcacatcnna gtanacagga gattcctccg caattacaag aatggntttn acgacantcc    540 tccctggnc tattaaaggg gattgcgtaa gntataagaa aaccgtctcg caccaaaaga    600
tacctagccn tacggcnaga tttgttcata nacttggta                           639
```

```
<210> SEQ ID NO 4
<211> LENGTH: 102
<212> TYPE: PRT
<213> ORGANISM: Impatiens balsamia
<220> FEATURE:
<221> NAME/KEY: UNSURE
<222> LOCATION: (88)
<223> OTHER INFORMATION: Xaa = ANY AMINO ACID

<400> SEQUENCE: 4
```

```
Val Glu Glu Ala Met Asn Gln Asn Lys Ile Phe Ile Leu Asp His His
  1               5                  10                  15

Asp Ser Leu Met Pro Tyr Leu Gly Arg Ile Asn Thr Thr Thr Thr Lys
             20                  25                  30

Thr Tyr Ala Ser Arg Thr Leu Leu Ile Leu Arg Lys Asp Gly Thr Leu
         35                  40                  45

Met Pro Leu Ala Ile Glu Leu Ser Leu Pro Asn Pro Arg Gly Asp Glu
     50                  55                  60

Tyr Gly Ala Ile Cys Lys Val Tyr Thr Pro Ala Gln His Gly Val Glu
 65                  70                  75                  80

Ala Ser Leu Trp Gln Leu Ala Xaa Ala Tyr Val Val Val Asn Asp Ser
                 85                  90                  95

Cys Ile His Glu Ser Val
            100
```

```
<210> SEQ ID NO 5
<211> LENGTH: 654
<212> TYPE: DNA
<213> ORGANISM: Zea mays
<220> FEATURE:
<221> NAME/KEY: unsure
<222> LOCATION: (4)
<223> OTHER INFORMATION: n = A, C, G, or T
<221> NAME/KEY: unsure
<222> LOCATION: (9)
<223> OTHER INFORMATION: n = A, C, G, or T
<221> NAME/KEY: unsure
<222> LOCATION: (35)
<223> OTHER INFORMATION: n = A, C, G, or T
<221> NAME/KEY: unsure
<222> LOCATION: (37)
<223> OTHER INFORMATION: n = A, C, G, or T
<221> NAME/KEY: unsure
<222> LOCATION: (89)
<223> OTHER INFORMATION: n = A, C, G, or T
<221> NAME/KEY: unsure
<222> LOCATION: (123)
<223> OTHER INFORMATION: n = A, C, G, or T
<221> NAME/KEY: unsure
```

```
<222> LOCATION: (135)
<223> OTHER INFORMATION: n = A, C, G, or T

<400> SEQUENCE: 5
aggngcacnc tcccggaccg gataccggcg gcacnancgg ctgccgagga tcagctgcag      60
cgccaccgag gaggtcagcg ggcgcccgng tcgtcccgtc accgtggaga ggatgctcac     120
ggngacggcg tcggnggagg cgtcgccggc catcgggcag atgtacttcc agcgcgccgt     180
cgacgacatc ggcgacctcc tcggcaagac gctgctgctc gagctcgtca gctccgagct     240
cgacgcaaag tcgggcgtgg agaaaacgcg ggtgacggcg tacgcgcaca agacgctgcg     300
ggagggccac tacgaggcgg agttcaaggt gccggcgtcg ttcgggccgg tgggcgcggt     360
gctggtggag aacgagcacc acaaggaggt cttcatcaag gagatcaagc tcgtcaccgg     420
cggcgacagc agcaccgccg tcaccttcga ctgcaactcc tgggtgcact ccaagttcga     480
caacccggag aagcgcatct tcttcaccct caagtcatac ctgccgtccg acacgcccaa     540
ggggctggag gacctgagga agaaagacct gcaggcgctg cgcggcgacg ggcacggcga     600
gcgcaaggtg ttcgagcgcg tctacgacta cgacgtgtac aacgaactgg gcga           654

<210> SEQ ID NO 6
<211> LENGTH: 147
<212> TYPE: PRT
<213> ORGANISM: Zea mays

<400> SEQUENCE: 6

Leu Leu Leu Glu Leu Val Ser Ser Glu Leu Asp Ala Lys Ser Gly Val
  1               5                  10                  15

Glu Lys Thr Arg Val Thr Ala Tyr Ala His Lys Thr Leu Arg Glu Gly
             20                  25                  30

His Tyr Glu Ala Glu Phe Lys Val Pro Ala Ser Phe Gly Pro Val Gly
         35                  40                  45

Ala Val Leu Val Glu Asn Glu His His Lys Glu Val Phe Ile Lys Glu
     50                  55                  60

Ile Lys Leu Val Thr Gly Gly Asp Ser Ser Thr Ala Val Thr Phe Asp
 65                  70                  75                  80

Cys Asn Ser Trp Val His Ser Lys Phe Asp Asn Pro Glu Lys Arg Ile
                 85                  90                  95

Phe Phe Thr Leu Lys Ser Tyr Leu Pro Ser Asp Thr Pro Lys Gly Leu
            100                 105                 110

Glu Asp Leu Arg Lys Lys Asp Leu Gln Ala Leu Arg Gly Asp Gly His
        115                 120                 125

Gly Glu Arg Lys Val Phe Glu Arg Val Tyr Asp Tyr Asp Val Tyr Asn
    130                 135                 140

Glu Leu Gly
145

<210> SEQ ID NO 7
<211> LENGTH: 597
<212> TYPE: DNA
<213> ORGANISM: Zea mays
<220> FEATURE:
<221> NAME/KEY: unsure
<222> LOCATION: (219)
<223> OTHER INFORMATION: n = A, C, G, or T
<221> NAME/KEY: unsure
<222> LOCATION: (225)
<223> OTHER INFORMATION: n = A, C, G, or T
<221> NAME/KEY: unsure
<222> LOCATION: (520)
```

```
<223> OTHER INFORMATION: n = A, C, G, or T
<221> NAME/KEY: unsure
<222> LOCATION: (558)
<223> OTHER INFORMATION: n = A, C, G, or T
<221> NAME/KEY: unsure
<222> LOCATION: (565)
<223> OTHER INFORMATION: n = A, C, G, or T
<221> NAME/KEY: unsure
<222> LOCATION: (582)
<223> OTHER INFORMATION: n = A, C, G, or T
<221> NAME/KEY: unsure
<222> LOCATION: (596)
<223> OTHER INFORMATION: n = A, C, G, or T

<400> SEQUENCE: 7
ggccgaggcg agcagccgtc gccgcctata tatcgcggcg cagggcagca ggagttccac    60
acttccatac acgcctgcct tgtgccttcc cttcccttgc cttgcttcgc ttattgccgg   120
cacatcacat cggcaggcga gggacggagc gagcagggaa gcccatccac cagccagcca   180
ccgcgttcct gagaagcgaa gagcgagaaa aggcgaaana gcggncatgt tctggcacgg   240
ggtcgcggac cggctgacgg gaaagaacaa ggaggcgtgg agcgagggca agatccgcgg   300
cacggtgagg ctggtcaaga aggaggtgct ggacgtcggc gacttcaacg cctcgctcct   360
cgacggcgtc cacaggatcc tcggctggga cgacggcgtc gccttcagct cgtcagcgcc   420
accgcgggcg accccagcaa cggggggccgt ggcaaggtgg ggaaggcggc gcacctggag   480
gaggcggtgg tgtcgctcaa gtcacggcgg acggggagan cgtgtaccgg gtgaagcttc   540
gagtgggacg agtcgcangg cattnccggg cgccgtctgg tnaggaacct gaagant      597

<210> SEQ ID NO 8
<211> LENGTH: 172
<212> TYPE: PRT
<213> ORGANISM: Zea mays
<220> FEATURE:
<221> NAME/KEY: UNSURE
<222> LOCATION: (73)
<223> OTHER INFORMATION: Xaa = ANY AMINO ACID
<221> NAME/KEY: UNSURE
<222> LOCATION: (75)
<223> OTHER INFORMATION: Xaa = ANY AMINO ACID

<400> SEQUENCE: 8
```

Ala Glu Ala Ser Ser Arg Arg Arg Leu Tyr Ile Ala Ala Gln Gly Ser
 1               5                  10                  15

Arg Ser Ser Thr Leu Pro Tyr Thr Pro Ala Leu Cys Leu Pro Phe Pro
            20                  25                  30

Cys Leu Ala Ser Leu Ile Ala Gly Thr Ser His Arg Gln Ala Arg Asp
        35                  40                  45

Gly Ala Ser Arg Glu Ala His Pro Pro Ala Ser His Arg Val Pro Glu
    50                  55                  60

Lys Arg Arg Ala Arg Lys Gly Glu Xaa Ala Xaa Met Phe Trp His Gly
65                  70                  75                  80

Val Ala Asp Arg Leu Thr Gly Lys Asn Lys Glu Ala Trp Ser Glu Gly
                85                  90                  95

Lys Ile Arg Gly Thr Val Arg Leu Val Lys Lys Glu Val Leu Asp Val
            100                 105                 110

Gly Asp Phe Asn Ala Ser Leu Leu Asp Gly Val His Arg Ile Leu Gly
        115                 120                 125

Trp Asp Asp Gly Val Ala Phe Ser Ser Ser Ala Pro Pro Arg Ala Thr
    130                 135                 140

Pro Ala Thr Gly Ala Val Ala Arg Trp Gly Arg Arg Arg Thr Trp Arg

-continued

```
                145                 150                 155                 160
            Arg Arg Trp Cys Arg Ser Ser His Gly Gly Arg Gly
                        165                 170

<210> SEQ ID NO 9
<211> LENGTH: 739
<212> TYPE: DNA
<213> ORGANISM: Zea mays
<220> FEATURE:
<221> NAME/KEY: unsure
<222> LOCATION: (15)
<223> OTHER INFORMATION: n = A, C, G, or T
<221> NAME/KEY: unsure
<222> LOCATION: (23)
<223> OTHER INFORMATION: n = A, C, G, or T
<221> NAME/KEY: unsure
<222> LOCATION: (80)
<223> OTHER INFORMATION: n = A, C, G, or T
<221> NAME/KEY: unsure
<222> LOCATION: (450)
<223> OTHER INFORMATION: n = A, C, G, or T
<221> NAME/KEY: unsure
<222> LOCATION: (455)
<223> OTHER INFORMATION: n = A, C, G, or T
<221> NAME/KEY: unsure
<222> LOCATION: (621)
<223> OTHER INFORMATION: n = A, C, G, or T
<221> NAME/KEY: unsure
<222> LOCATION: (667)
<223> OTHER INFORMATION: n = A, C, G, or T
<221> NAME/KEY: unsure
<222> LOCATION: (689)
<223> OTHER INFORMATION: n = A, C, G, or T
<221> NAME/KEY: unsure
<222> LOCATION: (704)
<223> OTHER INFORMATION: n = A, C, G, or T
<221> NAME/KEY: unsure
<222> LOCATION: (711)..(712)
<223> OTHER INFORMATION: n = A, C, G, or T

<400> SEQUENCE: 9
tctgcaaata ccccntttgg ttnctccaaa gagctagtag ttgcagttag ctctgccggt      60
agtggaaccg aagatgttcn cgaacatcgg aaagatcccc atcattggcg acctgacggg     120
cagcaacaag aatgcgcacc tcaagggcaa cgtggtgctc gtgcgcaaga ccgtgctcgg     180
cttggacgtc accagcatcg ccggctccct cctcgacggc gtcggcgagt tcctcggccg     240
cggcgtcacc tgccagctta tcagctccac cgtcgtcgac cctaacaacg gcaaccgcgg     300
gaagttgggc gcggaggcga gcctggagca gtggctgctg aacccgccgc cgcttctgtc     360
cagcgagaac cagttccgcg tcaccttcga ctgggaggtg gagaagcagg gcatcccggg     420
cgccatcatc gtcaagaaca accacgcctn cgagntcttc ctcaagacca tcaccctcaa     480
cgacgtcccc ggcacgggac catcgtcttc gtcgccaact catggatcta cccgcagtcc     540
aagtaccgct acaaccgcgt cttcttctcc aacgacacgt accttcccaa gccagatgcc     600
ggcggcgctg aagcctaccg ngacgacagc ttccggaacc tgaggggcga cgaccagcaa     660
ggcccgnacc aagaacacga accgcggtnt aaccggtacg acgnctacaa nngaaccttg     720
ggcctgcctg acaagcggg                                                  739

<210> SEQ ID NO 10
<211> LENGTH: 262
<212> TYPE: PRT
<213> ORGANISM: Zea mays
<220> FEATURE:
<221> NAME/KEY: UNSURE
<222> LOCATION: (14)
<223> OTHER INFORMATION: Xaa = ANY AMINO ACID
```

```
<221> NAME/KEY: UNSURE
<222> LOCATION: (137)
<223> OTHER INFORMATION: Xaa = ANY AMINO ACID
<221> NAME/KEY: UNSURE
<222> LOCATION: (139)
<223> OTHER INFORMATION: Xaa = ANY AMINO ACID
<221> NAME/KEY: UNSURE
<222> LOCATION: (194)
<221> NAME/KEY: UNSURE
<222> LOCATION: (201)
<223> OTHER INFORMATION: Xaa = ANY AMINO ACID
<221> NAME/KEY: UNSURE
<222> LOCATION: (258)
<223> OTHER INFORMATION: Xaa = ANY AMINO ACID

<400> SEQUENCE: 10
```

| | | | | | | | | | | | | | | |
|---|---|---|---|---|---|---|---|---|---|---|---|---|---|---|
| Leu | Gln | Leu | Ala | Leu | Pro | Val | Val | Glu | Pro | Lys | Met | Phe | Xaa | Asn | Ile |
| 1 | | | | 5 | | | | | 10 | | | | | 15 | |
| Gly | Lys | Ile | Pro | Ile | Ile | Gly | Asp | Leu | Thr | Gly | Ser | Asn | Lys | Asn | Ala |
| | | | 20 | | | | | 25 | | | | | 30 | | |
| His | Leu | Lys | Gly | Asn | Val | Val | Leu | Val | Arg | Lys | Thr | Val | Leu | Gly | Leu |
| | | 35 | | | | | 40 | | | | | 45 | | | |
| Asp | Val | Thr | Ser | Ile | Ala | Gly | Ser | Leu | Leu | Asp | Gly | Val | Gly | Glu | Phe |
| | 50 | | | | | 55 | | | | | 60 | | | | |
| Leu | Gly | Arg | Gly | Val | Thr | Cys | Gln | Leu | Ile | Ser | Ser | Thr | Val | Val | Asp |
| 65 | | | | | 70 | | | | | 75 | | | | | 80 |
| Pro | Asn | Asn | Gly | Asn | Arg | Gly | Lys | Leu | Gly | Ala | Glu | Ala | Ser | Leu | Glu |
| | | | | 85 | | | | | 90 | | | | | 95 | |
| Gln | Trp | Leu | Leu | Asn | Pro | Pro | Leu | Leu | Ser | Ser | Glu | Asn | Gln | Phe | |
| | | | 100 | | | | | 105 | | | | | 110 | | |
| Arg | Val | Thr | Phe | Asp | Trp | Glu | Val | Glu | Lys | Gln | Gly | Ile | Pro | Gly | Ala |
| | | 115 | | | | | 120 | | | | | 125 | | | |
| Ile | Ile | Val | Lys | Asn | Asn | His | Ala | Xaa | Glu | Xaa | Phe | Leu | Lys | Thr | Ile |
| | 130 | | | | | 135 | | | | | 140 | | | | |
| Thr | Leu | Asn | Asp | Val | Pro | Gly | Thr | Gly | Pro | Ser | Ser | Ser | Ser | Pro | Thr |
| 145 | | | | | 150 | | | | | 155 | | | | | 160 |
| His | Gly | Ser | Thr | Arg | Ser | Pro | Ser | Thr | Ala | Thr | Thr | Ala | Ser | Ser | Ser |
| | | | | 165 | | | | | 170 | | | | | 175 | |
| Pro | Thr | Thr | Arg | Thr | Phe | Pro | Ser | Gln | Met | Pro | Ala | Ala | Leu | Lys | Pro |
| | | | 180 | | | | | 185 | | | | | 190 | | |
| Thr | Xaa | Thr | Thr | Ala | Ser | Gly | Thr | Xaa | Thr | Ile | Val | Phe | Val | Ala | Asn |
| | | 195 | | | | | 200 | | | | | 205 | | | |
| Ser | Trp | Ile | Tyr | Pro | Gln | Ser | Lys | Tyr | Arg | Tyr | Asn | Arg | Val | Phe | Phe |
| | 210 | | | | | 215 | | | | | 220 | | | | |
| Ser | Asn | Asp | Thr | Tyr | Leu | Pro | Lys | Pro | Asp | Ala | Gly | Gly | Ala | Glu | Ala |
| 225 | | | | | 230 | | | | | 235 | | | | | 240 |
| Tyr | Arg | Asp | Asp | Ser | Phe | Arg | Asn | Leu | Arg | Gly | Asp | Asp | Gln | Gln | Gly |
| | | | | 245 | | | | | 250 | | | | | 255 | |
| Pro | Xaa | Gln | Glu | His | Glu | | | | | | | | | | |
| | | | 260 | | | | | | | | | | | | |

```
<210> SEQ ID NO 11
<211> LENGTH: 2929
<212> TYPE: DNA
<213> ORGANISM: Momordica charantia

<400> SEQUENCE: 11
gcacgaggag aatgtttggg attgggaaga gtatcataga gggcgccgtg aacactaccg      60
gcgacctcgc cggctccgtc atcaatgccg gcggcaatat tgtagggcgt gtcaccaata     120
```

-continued

```
tcggcgggaa gaagatcaaa gggacggtgg ttcttatgag aagcaatgtt ttggacttca    180
ccgaatttca ttcctcactt cttgacggcg tcactgagct cttgggcggc ggaatttcat    240
tgcaacttat cagtgctact cacgcttcca acgactcgcg agggaaagtt ggaaaggggg    300
cgtttctgga gaggtggctg acttcagttc cgccactgtt cgctggagag tctgtgtttc    360
aagtgaactt tgattgggaa gagaactttg gatttccagg agctttcttc ataaaaaatg    420
ggcacaccag tgagttcttc ctcaagtctg taactctgga ggatgttcct ggctttggaa    480
gggtccattt tgactgcaac tcatgggttt acccttctcg aagatacaag aaagatcgca    540
ttttctttgc caaccataca tgccttccaa tcgatacacc ggattcactt cgtaagtata    600
gagaggagga gttgttgaac ctcagaggag atggaacagg agagcgtaaa gaatgggata    660
gaatttatga ctatgatgtt tacaacgacc tctgtgatcc aaatggtggt cctaaccttg    720
ttcgtcctat tcttggaggg agtgatcagt acccttaccc tcgtagaggg aggacaggaa    780
gaccaccggc tagaaaagat cacaagtacg agagcagatt gtcggatgtg atgagcttaa    840
acatttacgt accgagagac gaaaatttcg gacacttgaa gatggcggat ttccttggga    900
atacgttgaa ggtactttct acatctatcc aaccaggact tgaatctata tttgattcaa    960
ccccaggaga atttgacaaa ttcaaagaag tagacgatct cttttgaacga gggtttccca   1020
ttccattgaa tatttttaag aacctcacag aggacctcgc cccacccctc tttaaagcat   1080
ttctgaggag tgatggtgaa agattcctca aatatccaac tccccaagtt atcaaagata   1140
acaagttagg gtggaggaca gatgaagaat ttgccagaga aatgatagcg ggagtcaatc   1200
ctttgatcat tcgtcgtctt gaagtttttc caccattgag taagttggac cctcatgttt   1260
atgggaatca aaacagtaca atgacggaag aacaaataaa gcatggttta gatggactca   1320
cggttgatga ggcaatcaag gaaaataagc tctacatatt ggatcaccat gatgcattga   1380
tgccatatct taggagaata aattcaacat ctacaaaaac atatgccaca gaacacttc    1440
tcttttttgaa agatgacagt actttgaagc cattggctat tgagttgagc ttgccacacc   1500
cgcaaggaga tgaacatggt gccattagca aactatactt tccagctgaa ggaagagttg   1560
agagtgccat ttggcaactg gccaaagctt atgtagctgt taatgatagt gggtaccatc   1620
aacttaacag tcactggtta cacactcatg cagtgctgga gccttttgtt atcacaacac   1680
atcgacgatt gagtgtgctc catccaattc acaagttact tgctcctcat tacaaagaca   1740
ccatgtttat aaatgcatct gcaaggcaag ttttgattaa cgcgggtggt cttattgaat   1800
cgactcagtt tccggcaaag tatgctatgg agctgtcatc ttacatatat aaggaatgga   1860
agttccccga tgaagcactc cctactaatc tcattaagag aggagtagca attgaggact   1920
caggctctcc ccatggagtt cgacttctaa taaacgatta ccccttttgct gttgatgggc   1980
tcgagatttg gtcagccatc aaaacatggg tcacagatta ctgctccctc tactacaaag   2040
acgacgacgc aattcgaaat gatgtcgagc tccaatcatg gtggaaagaa ctcagagaaa   2100
aagtcatac agacaagaaa gacgagccat ggtggcccaa aatgcaaact ttttcagagt   2160
taattgaatc atgcaccata atcatatgga tttcttcagc ccttcacgca gcagtcaatt   2220
ttgggcaata cccttatgga ggctacgttc ccaacagacc aaccacaagc agaagattca   2280
tgccagaagt aggcactgca gagtacaaag aagttgaatc aaaccctgaa aaggcctttc   2340
taagaacaat cagctcgcaa atagtggctc ttcttggcct ctcgataatt gaaatattgt   2400
caaagcacgc ttctgacgag gtctacctcg ggcaaagagc cagcattgag tggacatcag   2460
```

```
acaaatctgc aattgaagcc tttgagaaat ttgggaaaga gctgtttgaa gttgaggata    2520
gaattatgcg aaggaatcaa gatgtgaact tgaagaatcg agctgggcct gtcaatatgc    2580
cttacacttt gcttgttcca tcgagtactg agggactcac tgggagagga attcccaaca    2640
gtatctccat ataaatgaag aagtgttttc atgggaggtg tctatattgt gtaatttgaa    2700
ggtcacaaat tacattctaa ttaagctgcc cattttggag agaataatga ccatgtttat    2760
gtttttgaga agactttagg ctttggattt ccaagaatgc aaaaggttat gtacttgtga    2820
attcctatct aatgaataaa agttgtgttt taataatgat attcaattac cctaccccca    2880
aaaaaaaaaa aaaaaaaaaa aaaaaaaaaa aaaaaaaaa aaaaaaaa                  2929
```

<210> SEQ ID NO 12
<211> LENGTH: 880
<212> TYPE: PRT
<213> ORGANISM: Momordica charantia

<400> SEQUENCE: 12

```
Met Phe Gly Ile Gly Lys Ser Ile Ile Glu Gly Ala Val Asn Thr Thr
 1               5                  10                  15

Gly Asp Leu Ala Gly Ser Val Ile Asn Ala Gly Asn Ile Val Gly
            20                  25                  30

Arg Val Thr Asn Ile Gly Gly Lys Lys Ile Lys Gly Thr Val Val Leu
        35                  40                  45

Met Arg Ser Asn Val Leu Asp Phe Thr Glu Phe His Ser Ser Leu Leu
    50                  55                  60

Asp Gly Val Thr Glu Leu Leu Gly Gly Ile Ser Leu Gln Leu Ile
65                  70                  75                  80

Ser Ala Thr His Ala Ser Asn Asp Ser Arg Gly Lys Val Gly Lys Gly
                85                  90                  95

Ala Phe Leu Glu Arg Trp Leu Thr Ser Val Pro Pro Leu Phe Ala Gly
            100                 105                 110

Glu Ser Val Phe Gln Val Asn Phe Asp Trp Glu Glu Asn Phe Gly Phe
        115                 120                 125

Pro Gly Ala Phe Phe Ile Lys Asn Gly His Thr Ser Glu Phe Phe Leu
    130                 135                 140

Lys Ser Val Thr Leu Glu Asp Val Pro Gly Phe Gly Arg Val His Phe
145                 150                 155                 160

Asp Cys Asn Ser Trp Val Tyr Pro Ser Arg Arg Tyr Lys Lys Asp Arg
                165                 170                 175

Ile Phe Phe Ala Asn His Thr Cys Leu Pro Ile Asp Thr Pro Asp Ser
            180                 185                 190

Leu Arg Lys Tyr Arg Glu Glu Leu Leu Asn Leu Arg Gly Asp Gly
        195                 200                 205

Thr Gly Glu Arg Lys Glu Trp Asp Arg Ile Tyr Asp Tyr Asp Val Tyr
    210                 215                 220

Asn Asp Leu Cys Asp Pro Asn Gly Gly Pro Asn Leu Val Arg Pro Ile
225                 230                 235                 240

Leu Gly Gly Ser Asp Gln Tyr Pro Tyr Pro Arg Arg Gly Arg Thr Gly
                245                 250                 255

Arg Pro Pro Ala Arg Lys Asp His Lys Tyr Glu Ser Arg Leu Ser Asp
            260                 265                 270

Val Met Ser Leu Asn Ile Tyr Val Pro Arg Asp Glu Asn Phe Gly His
        275                 280                 285

Leu Lys Met Ala Asp Phe Leu Gly Asn Thr Leu Lys Val Leu Ser Thr
```

-continued

```
            290                 295                 300
Ser Ile Gln Pro Gly Leu Glu Ser Ile Phe Asp Ser Thr Pro Gly Glu
305                 310                 315                 320

Phe Asp Lys Phe Lys Glu Val Asp Asp Leu Phe Glu Arg Gly Phe Pro
                325                 330                 335

Ile Pro Leu Asn Ile Phe Lys Asn Leu Thr Glu Asp Leu Ala Pro Pro
                340                 345                 350

Leu Phe Lys Ala Phe Leu Arg Ser Asp Gly Glu Arg Phe Leu Lys Tyr
                355                 360                 365

Pro Thr Pro Gln Val Ile Lys Asp Asn Lys Leu Gly Trp Arg Thr Asp
    370                 375                 380

Glu Glu Phe Ala Arg Glu Met Ile Ala Gly Val Asn Pro Leu Ile Ile
385                 390                 395                 400

Arg Arg Leu Glu Val Phe Pro Pro Leu Ser Lys Leu Asp Pro His Val
                405                 410                 415

Tyr Gly Asn Gln Asn Ser Thr Met Thr Glu Glu Gln Ile Lys His Gly
                420                 425                 430

Leu Asp Gly Leu Thr Val Asp Glu Ala Ile Lys Glu Asn Lys Leu Tyr
                435                 440                 445

Ile Leu Asp His His Asp Ala Leu Met Pro Tyr Leu Arg Arg Ile Asn
    450                 455                 460

Ser Thr Ser Thr Lys Thr Tyr Ala Thr Arg Thr Leu Leu Phe Leu Lys
465                 470                 475                 480

Asp Asp Ser Thr Leu Lys Pro Leu Ala Ile Glu Leu Ser Leu Pro His
                485                 490                 495

Pro Gln Gly Asp Glu His Gly Ala Ile Ser Lys Leu Tyr Phe Pro Ala
                500                 505                 510

Glu Gly Arg Val Glu Ser Ala Ile Trp Gln Leu Ala Lys Ala Tyr Val
                515                 520                 525

Ala Val Asn Asp Ser Gly Tyr His Gln Leu Asn Ser His Trp Leu His
    530                 535                 540

Thr His Ala Val Leu Glu Pro Phe Val Ile Thr Thr His Arg Arg Leu
545                 550                 555                 560

Ser Val Leu His Pro Ile His Lys Leu Leu Ala Pro His Tyr Lys Asp
                565                 570                 575

Thr Met Phe Ile Asn Ala Ser Ala Arg Gln Val Leu Ile Asn Ala Gly
                580                 585                 590

Gly Leu Ile Glu Ser Thr Gln Phe Pro Ala Lys Tyr Ala Met Glu Leu
                595                 600                 605

Ser Ser Tyr Ile Tyr Lys Glu Trp Lys Phe Pro Asp Glu Ala Leu Pro
    610                 615                 620

Thr Asn Leu Ile Lys Arg Gly Val Ala Ile Glu Asp Ser Gly Ser Pro
625                 630                 635                 640

His Gly Val Arg Leu Leu Ile Asn Asp Tyr Pro Phe Ala Val Asp Gly
                645                 650                 655

Leu Glu Ile Trp Ser Ala Ile Lys Thr Trp Val Thr Asp Tyr Cys Ser
                660                 665                 670

Leu Tyr Tyr Lys Asp Asp Ala Ile Arg Asn Asp Val Glu Leu Gln
                675                 680                 685

Ser Trp Trp Lys Glu Leu Arg Glu Lys Gly His Thr Asp Lys Lys Asp
    690                 695                 700

Glu Pro Trp Trp Pro Lys Met Gln Thr Phe Ser Glu Leu Ile Glu Ser
705                 710                 715                 720
```

-continued

```
Cys Thr Ile Ile Ile Trp Ile Ser Ser Ala Leu His Ala Ala Val Asn
                725                 730                 735
Phe Gly Gln Tyr Pro Tyr Gly Gly Tyr Val Pro Asn Arg Pro Thr Thr
            740                 745                 750
Ser Arg Arg Phe Met Pro Glu Val Gly Thr Ala Glu Tyr Lys Glu Val
        755                 760                 765
Glu Ser Asn Pro Glu Lys Ala Phe Leu Arg Thr Ile Ser Ser Gln Ile
    770                 775                 780
Val Ala Leu Leu Gly Leu Ser Ile Ile Glu Ile Leu Ser Lys His Ala
785                 790                 795                 800
Ser Asp Glu Val Tyr Leu Gly Gln Arg Ala Ser Ile Glu Trp Thr Ser
                805                 810                 815
Asp Lys Ser Ala Ile Glu Ala Phe Glu Lys Phe Gly Lys Glu Leu Phe
            820                 825                 830
Glu Val Glu Asp Arg Ile Met Arg Arg Asn Gln Asp Val Asn Leu Lys
        835                 840                 845
Asn Arg Ala Gly Pro Val Asn Met Pro Tyr Thr Leu Leu Val Pro Ser
    850                 855                 860
Ser Thr Glu Gly Leu Thr Gly Arg Gly Ile Pro Asn Ser Ile Ser Ile
865                 870                 875                 880
```

<210> SEQ ID NO 13
<211> LENGTH: 1577
<212> TYPE: DNA
<213> ORGANISM: Impatiens balsamia

<400> SEQUENCE: 13

```
gcacgaggtt gaagaggcaa tgaatcaaaa caagattttc atattagatc accatgatag     60
tttgatgcca tacttgggga gaatcaacac aaccaccaca aagacttatg cttcaaggac    120
tcttcttatc cttaggaaag atgggacttt gatgccatta gccattgagc taagcctgcc    180
caacccaaga ggagatgaat atggtgccat atgcaaagtc tacaccccgg ctcaacatgg    240
tgtagaagcc tcccttttgc agcttgctaa agcctatgtc gtggttaacg actctggtat    300
ccacgaactc gtcagtcatt ggttgaacac gcatgcagtg attgagccat tgtaatcgc    360
gacaaacaga caactgagcg tacttcatcc gatacaaaag ttgttgcacc ctcattttcg    420
agacacgatg aacattaatg caatcgcaag gaatgtacta atcaacgcgg tggagttat    480
tgagaatacg ttttcacat caaagtatcg catggagatg tcatccgcaa tttacaagaa    540
ttggattttc accgaccagt ctctccccgt ggaccttatt aaaggggga ttgcggttaa    600
ggatgataaa gaaaacgcg tcttcgcct actcatagag gattacccgt atgcggttga    660
cgggctagag atatggtttg cgataaagac atgggtcgag gactattgcg acttctacta    720
caaaggcgac gaggcagtta agaatgacac cgagctccaa gcatggtgga aggagctaaa    780
ggaagttggc cacggagaca aaggaatga accgtggtgg cccaaaatgg aaacaaggaa    840
agatctattg gagacatgca caatcatcat atgggtggca tctgcccttc atgcagccct    900
gaatttcggg caatacccat atggcggata ccatcctaac cggcccacaa atagccgaag    960
gctaatgccc gaagtgggta gtcctgaatt cgaggagttg aagacaaatc cggaccaaat   1020
tttgttgaaa acgttgagtt ctaaagctca aactcttctc gaggttgcta tcattgagat   1080
tttgtcgagg catacgtcgg atgaggtcta tctcgggcag agggacacgc ccgagtggac   1140
caaagatgaa gagccactta agccttcgaa taagtttgga aaaaagttag cagaaattga   1200
```

-continued

```
ggtaaggatt attgagatga acaatgatga gagtctcaag aatagaaatg gaccagtcaa    1260
aataccttat actttgctat ttccaaccag ttcaagtggg ctaactggga agggcatatc    1320
aaatagtgtg tctatttgaa tgatccaaac tggctagcat taatcatata tataatatat    1380
taatatattt cttttcattt ctaaaaatgt attaatttta gaggttattg tttaaacatt    1440
ataattgtct ttattgtttg tattaaaatg tatcccacta tgtaattata tacatattta    1500
tgaaataaat gtatttgtat ggtaaaaaaa aaaaaaaaaa aaaaaaaaaa aaaaaaaaaa    1560
aaaaaaaaaa aaaaaaa                                                   1577
```

<210> SEQ ID NO 14
<211> LENGTH: 445
<212> TYPE: PRT
<213> ORGANISM: Impatiens balsamia

<400> SEQUENCE: 14

```
His Glu Val Glu Glu Ala Met Asn Gln Asn Lys Ile Phe Ile Leu Asp
  1               5                  10                  15

His His Asp Ser Leu Met Pro Tyr Leu Gly Arg Ile Asn Thr Thr Thr
             20                  25                  30

Thr Lys Thr Tyr Ala Ser Arg Thr Leu Leu Ile Leu Arg Lys Asp Gly
         35                  40                  45

Thr Leu Met Pro Leu Ala Ile Glu Leu Ser Leu Pro Asn Pro Arg Gly
     50                  55                  60

Asp Glu Tyr Gly Ala Ile Cys Lys Val Tyr Thr Pro Ala Gln His Gly
 65                  70                  75                  80

Val Glu Ala Ser Leu Trp Gln Leu Ala Lys Ala Tyr Val Val Val Asn
                 85                  90                  95

Asp Ser Gly Ile His Glu Leu Val Ser His Trp Leu Asn Thr His Ala
            100                 105                 110

Val Ile Glu Pro Phe Val Ile Ala Thr Asn Arg Gln Leu Ser Val Leu
        115                 120                 125

His Pro Ile Gln Lys Leu Leu His Pro His Phe Arg Asp Thr Met Asn
    130                 135                 140

Ile Asn Ala Ile Ala Arg Asn Val Leu Ile Asn Ala Gly Gly Val Ile
145                 150                 155                 160

Glu Asn Thr Phe Phe Thr Ser Lys Tyr Ser Met Glu Met Ser Ser Ala
                165                 170                 175

Ile Tyr Lys Asn Trp Ile Phe Thr Asp Gln Ser Leu Pro Val Asp Leu
            180                 185                 190

Ile Lys Arg Gly Ile Ala Val Lys Asp Lys Glu Lys Arg Gly Leu
        195                 200                 205

Arg Leu Leu Ile Glu Asp Tyr Pro Tyr Ala Val Asp Gly Leu Glu Ile
    210                 215                 220

Trp Phe Ala Ile Lys Thr Trp Val Glu Asp Tyr Cys Asp Phe Tyr Tyr
225                 230                 235                 240

Lys Gly Asp Glu Ala Val Lys Asn Asp Thr Glu Leu Gln Ala Trp Trp
                245                 250                 255

Lys Glu Leu Lys Glu Val Gly His Gly Asp Lys Arg Asn Glu Pro Trp
            260                 265                 270

Trp Pro Lys Met Glu Thr Arg Lys Asp Leu Leu Glu Thr Cys Thr Ile
        275                 280                 285

Ile Ile Trp Val Ala Ser Ala Leu His Ala Ala Leu Asn Phe Gly Gln
    290                 295                 300
```

```
Tyr Pro Tyr Gly Gly Tyr His Pro Asn Arg Pro Thr Asn Ser Arg Arg
305                 310                 315                 320

Leu Met Pro Glu Val Gly Ser Pro Glu Phe Glu Leu Lys Thr Asn
            325                 330                 335

Pro Asp Gln Ile Leu Leu Lys Thr Leu Ser Ser Lys Ala Gln Thr Leu
            340                 345                 350

Leu Glu Val Ala Ile Ile Glu Ile Leu Ser Arg His Thr Ser Asp Glu
            355                 360                 365

Val Tyr Leu Gly Gln Arg Asp Thr Pro Glu Trp Thr Lys Asp Glu Glu
    370                 375                 380

Pro Leu Lys Ala Phe Asp Lys Phe Gly Lys Lys Leu Ala Glu Ile Glu
385                 390                 395                 400

Val Arg Ile Ile Glu Met Asn Asn Asp Glu Ser Leu Lys Asn Arg Asn
                405                 410                 415

Gly Pro Val Lys Ile Pro Tyr Thr Leu Leu Phe Pro Thr Ser Ser Ser
            420                 425                 430

Gly Leu Thr Gly Lys Gly Ile Ser Asn Ser Val Ser Ile
            435                 440                 445
```

<210> SEQ ID NO 15
<211> LENGTH: 3134
<212> TYPE: DNA
<213> ORGANISM: Zea mays

<400> SEQUENCE: 15

```
ccacgcgtcc  ggccgaggcg  agcagccgtc  gccgcctata  tatcgcggcg  cagggcagca    60
ggagttccac  acttccatac  acgcctgcct  tgtgccttcc  cttcccttgc  cttgcttcgc   120
ttattgccgg  cacatcacat  cggcaggcga  gggacggagc  gagcagggaa  gcccatccac   180
cagccagcca  ccgcgttcct  gagaagcgag  gagcgagaaa  agcgaagagc  ggccatgttc   240
tggcacgggg  tcgcggaccg  gctgacggga  aagaacaagg  aggcgtggag  cgagggcaag   300
atccgcggca  cggtgaggct  ggtcaagaag  gaggtgctgg  acgtcggcga  cttcaacgcc   360
tcgctcctcg  acgcgtccca  caggatcctc  ggctgggacg  acgcgtcgc  cttccagctc   420
gtcagcgcca  ccgcggccga  ccccagcaac  gggggccgtg  gcaaggtggg  gaaggcggcg   480
cacctggagg  aggcggtggt  gtcgctcaag  tccacggcgg  acggggagac  cgtgtaccgg   540
gtgagcttcg  agtgggacga  gtcgcagggc  atcccgggcg  ccgtcctggt  caggaacctg   600
cagcacgccg  agttcttcct  caagacgctc  accctcgagg  gcgtcccagg  caagggcacc   660
gtcgtcttcg  tcgccaactc  gtgggtctac  ccgcacaagc  tctactccca  ggaacgcatc   720
ttcttcgcca  acgaccccta  tctgccgagc  aaaatgccgg  cggcgttggt  gccttatcgg   780
caagatgagc  tcaagattct  ccgtggcgac  gataatcctg  gaccatacca  ggagcatgat   840
cgcgtctacc  gttacgacta  ctacaatgac  cttggtgatc  cgacaagggc  gaagagcac   900
gctcggccga  tcctcggtgg  cagccaagaa  cacccgtatc  ccgtcgctg  cagaactggc   960
cggcacccaa  caaagaaaga  cccaaattcg  gagagcaggc  ttttcctgct  gaacctgaac  1020
atctacgtcc  gcgtgacga  acgctttggg  catctcaaga  tgtcggactt  ccttgggtac  1080
tcgctgaaga  cgatcatcga  ggctgttctt  ccaacactgg  ggactttcgt  cgatgacacg  1140
cccaaggagt  tcgattcgtt  tgaggatatc  ctcgggctct  acgagctggg  cccagaggca  1200
cccaacaacc  cactgatagc  agagatcagg  aagaagatcc  ccagcgagtt  ccttcgaagc  1260
attctgccga  acggtagcca  tgaccacccg  ctaaagatgc  cccttccaaa  tgtcatcaaa  1320
```

-continued

```
tcagatgtgt tgaaaaaggc tccggagttt aagtttggct ggaggactga cgaagagttc    1380
gcgagagaga cacttgcagg cgtgaaccca gtaatcatca aacgtctgac ggagttcccc    1440
gctaaaagca ccctggaccc aaggcagtac ggagaccaca ccagcaagat cactgaagct    1500
cacatccggc ataacatggg aggcctgtcg gtgcagaacg cactgaggaa caagaggctc    1560
ttcatcctag accaccatga ccatttcatg ccgtacctcg acgagatcaa cgagctggag    1620
gggaacttca tctacgccag caggacccta ctgttcctga aggacgatgg cacgctgaag    1680
cccctggcca tcgagctgag cctgccccac cctgacggcc agcagcgcgg cgcggtcagc    1740
aaggtgtaca ccccggctca caccggcgtc gagggccacg tctggcagct cgccaaggct    1800
tatgcctgcg taaacgactc tgcctggcat cagctgatca gccactggct gaacacgcac    1860
gcggtgatcg agccgttcgt aatcgcgaca accggcagc tcagcgtggt gcatcccgtg     1920
cacaagctgc tgagcccgca ctaccgtgac acgctgaaca tcaacgccct ggcacgccag    1980
acactcatca acgccggcgg cgtcttcgag cgcaccgtgt tccctgcaaa gtacgcgctg    2040
gggatgtcgg cagacgtgta caagagctgg aatttcaacg agcaggctct cccagcagat    2100
ctcgtcaaga gaggtgtggc tgtgccggac cagtcaagcc catatggtgt ccgactgctg    2160
atcaaggact accctatgc cgttgacggg ctcgtcatct ggtgggcgat cgagcggtgg     2220
gtcaaggagt acctggacat ctactaccct aacgacggcg agctccagcg tgacgtggag    2280
ctgcaggcgt ggtggaagga ggtgcgtgag gaggcgcacg gcgacctcaa ggaccgagac    2340
tggtggccca ggatggacac cgtccagcag ctggctaggg cgtgcacgac catcatctgg    2400
gtggcatccg cgctgcacgc ggctgtcaac tttgggcagt acccatacgc cgggtacctc    2460
ccgaaccggc cgacggccag ccggcgcccg atgccggagc caggcagcca cgactacaag    2520
aagctgggag cggggcagaa ggaggcggac atggtgttca tccgcaccat caccagccag    2580
ttccagacca tcctgggcat ctcgctcatc gagatcctct ccaagcactc ctccgacgag    2640
gtgtacctcg ccagcgtga cgagcctgat cgctggacgt cagacgccaa ggcgctggat     2700
gcgttcaaaa gattcgggag ccggctggtg cagattgaga atcggatcaa gacgatgaac    2760
gacagtccgg acttgaagaa ccggaagggg cctgtggaaa tgccgtacat gctgctgtac    2820
cccaacacgt cggacgttac cggcgagaag gccgagggcc ttactgccat gggcattccc    2880
aacagcatct ccatatgagc ctgggcagat tgtgtctcgt agtaaattgt tgtgctgcgc    2940
cgtgcgatgt gtttcttcat tggttttgtc agtctcaggg tagggatgg agatcatacc      3000 atgatctttg tagggttgag agaggagtcc acgcttgaat attgttgtca tgtatgtaat    3060
tcttggttaa taataaagtt cgtcagttca tttcttaaaa aaaacaaaa aaaaaaaaa      3120 aaaaaaaaaa aaag                                                       3134
```

<210> SEQ ID NO 16
<211> LENGTH: 887
<212> TYPE: PRT
<213> ORGANISM: Zea mays

<400> SEQUENCE: 16

```
Met Phe Trp His Gly Val Ala Asp Arg Leu Thr Gly Lys Asn Lys Glu
  1               5                  10                  15

Ala Trp Ser Glu Gly Lys Ile Arg Gly Thr Val Arg Leu Val Lys Lys
             20                  25                  30

Glu Val Leu Asp Val Gly Asp Phe Asn Ala Ser Leu Leu Asp Gly Val
         35                  40                  45
```

```
His Arg Ile Leu Gly Trp Asp Asp Gly Val Ala Phe Gln Leu Val Ser
     50                  55                  60
Ala Thr Ala Ala Asp Pro Ser Asn Gly Gly Arg Gly Lys Val Gly Lys
 65                  70                  75                  80
Ala Ala His Leu Glu Glu Ala Val Val Ser Leu Lys Ser Thr Ala Asp
                 85                  90                  95
Gly Glu Thr Val Tyr Arg Val Ser Phe Glu Trp Asp Glu Ser Gln Gly
                100                 105                 110
Ile Pro Gly Ala Val Leu Val Arg Asn Leu Gln His Ala Glu Phe Phe
            115                 120                 125
Leu Lys Thr Leu Thr Leu Glu Gly Val Pro Gly Lys Gly Thr Val Val
    130                 135                 140
Phe Val Ala Asn Ser Trp Val Tyr Pro His Lys Leu Tyr Ser Gln Glu
145                 150                 155                 160
Arg Ile Phe Phe Ala Asn Asp Thr Tyr Leu Pro Ser Lys Met Pro Ala
                165                 170                 175
Ala Leu Val Pro Tyr Arg Gln Asp Glu Leu Lys Ile Leu Arg Gly Asp
            180                 185                 190
Asp Asn Pro Gly Pro Tyr Gln Glu His Asp Arg Val Tyr Arg Tyr Asp
    195                 200                 205
Tyr Tyr Asn Asp Leu Gly Asp Pro Asp Lys Gly Glu Glu His Ala Arg
    210                 215                 220
Pro Ile Leu Gly Gly Ser Gln Glu His Pro Tyr Pro Arg Arg Cys Arg
225                 230                 235                 240
Thr Gly Arg His Pro Thr Lys Lys Asp Pro Asn Ser Glu Ser Arg Leu
                245                 250                 255
Phe Leu Leu Asn Leu Asn Ile Tyr Val Pro Arg Asp Glu Arg Phe Gly
            260                 265                 270
His Leu Lys Met Ser Asp Phe Leu Gly Tyr Ser Leu Lys Thr Ile Ile
    275                 280                 285
Glu Ala Val Leu Pro Thr Leu Gly Thr Phe Val Asp Asp Thr Pro Lys
290                 295                 300
Glu Phe Asp Ser Phe Glu Asp Ile Leu Gly Leu Tyr Glu Leu Gly Pro
                305                 310                 315                 320
Glu Ala Pro Asn Asn Pro Leu Ile Ala Glu Ile Arg Lys Lys Ile Pro
                325                 330                 335
Ser Glu Phe Leu Arg Ser Ile Leu Pro Asn Gly Ser His Asp His Pro
            340                 345                 350
Leu Lys Met Pro Leu Pro Asn Val Ile Lys Ser Asp Val Leu Lys Lys
    355                 360                 365
Ala Pro Glu Phe Lys Phe Gly Trp Arg Thr Asp Glu Glu Phe Ala Arg
370                 375                 380
Glu Thr Leu Ala Gly Val Asn Pro Val Ile Ile Lys Arg Leu Thr Glu
385                 390                 395                 400
Phe Pro Ala Lys Ser Thr Leu Asp Pro Arg Gln Tyr Gly Asp His Thr
                405                 410                 415
Ser Lys Ile Thr Glu Ala His Ile Arg His Asn Met Gly Gly Leu Ser
            420                 425                 430
Val Gln Asn Ala Leu Arg Asn Lys Arg Leu Phe Ile Leu Asp His His
    435                 440                 445
Asp His Phe Met Pro Tyr Leu Asp Glu Ile Asn Glu Leu Glu Gly Asn
450                 455                 460
Phe Ile Tyr Ala Ser Arg Thr Leu Leu Phe Leu Lys Asp Asp Gly Thr
```

```
                465                 470                 475                 480
Leu Lys Pro Leu Ala Ile Glu Leu Ser Leu Pro His Pro Asp Gly Gln
                    485                 490                 495
Gln Arg Gly Ala Val Ser Lys Val Tyr Thr Pro Ala His Thr Gly Val
                500                 505                 510
Glu Gly His Val Trp Gln Leu Ala Lys Ala Tyr Ala Cys Val Asn Asp
            515                 520                 525
Ser Ala Trp His Gln Leu Ile Ser His Trp Leu Asn Thr His Ala Val
        530                 535                 540
Ile Glu Pro Phe Val Ile Ala Thr Asn Arg Gln Leu Ser Val Val His
545                 550                 555                 560
Pro Val His Lys Leu Leu Ser Pro His Tyr Arg Asp Thr Leu Asn Ile
                565                 570                 575
Asn Ala Leu Ala Arg Gln Thr Leu Ile Asn Ala Gly Val Phe Glu
            580                 585                 590
Arg Thr Val Phe Pro Ala Lys Tyr Ala Leu Gly Met Ser Ala Asp Val
        595                 600                 605
Tyr Lys Ser Trp Asn Phe Asn Glu Gln Ala Leu Pro Ala Asp Leu Val
    610                 615                 620
Lys Arg Gly Val Ala Val Pro Asp Gln Ser Ser Pro Tyr Gly Val Arg
625                 630                 635                 640
Leu Leu Ile Lys Asp Tyr Pro Tyr Ala Val Asp Gly Leu Val Ile Trp
                645                 650                 655
Trp Ala Ile Glu Arg Trp Val Lys Glu Tyr Leu Asp Ile Tyr Tyr Pro
            660                 665                 670
Asn Asp Gly Glu Leu Gln Arg Asp Val Glu Leu Gln Ala Trp Trp Lys
        675                 680                 685
Glu Val Arg Glu Glu Ala His Gly Asp Leu Lys Asp Arg Asp Trp Trp
    690                 695                 700
Pro Arg Met Asp Thr Val Gln Gln Leu Ala Arg Ala Cys Thr Thr Ile
705                 710                 715                 720
Ile Trp Val Ala Ser Ala Leu His Ala Ala Val Asn Phe Gly Gln Tyr
                725                 730                 735
Pro Tyr Ala Gly Tyr Leu Pro Asn Arg Pro Thr Ala Ser Arg Arg Pro
            740                 745                 750
Met Pro Glu Pro Gly Ser His Asp Tyr Lys Lys Leu Gly Ala Gly Gln
        755                 760                 765
Lys Glu Ala Asp Met Val Phe Ile Arg Thr Ile Thr Ser Gln Phe Gln
    770                 775                 780
Thr Ile Leu Gly Ile Ser Leu Ile Glu Ile Leu Ser Lys His Ser Ser
785                 790                 795                 800
Asp Glu Val Tyr Leu Gly Gln Arg Asp Glu Pro Asp Arg Trp Thr Ser
                805                 810                 815
Asp Ala Lys Ala Leu Asp Ala Phe Lys Arg Phe Gly Ser Arg Leu Val
            820                 825                 830
Gln Ile Glu Asn Arg Ile Lys Thr Met Asn Asp Ser Pro Asp Leu Lys
        835                 840                 845
Asn Arg Lys Gly Pro Val Glu Met Pro Tyr Met Leu Leu Tyr Pro Asn
    850                 855                 860
Thr Ser Asp Val Thr Gly Glu Lys Ala Glu Gly Leu Thr Ala Met Gly
865                 870                 875                 880
Ile Pro Asn Ser Ile Ser Ile
                885
```

<210> SEQ ID NO 17
<211> LENGTH: 1438
<212> TYPE: DNA
<213> ORGANISM: Zea mays

<400> SEQUENCE: 17

| | | | | | |
|---|---|---|---|---|---|
| ggtccggctc | ccggcggcac | gtgcggctgc | cgaggatcag | ctgcagcgcc | accgaggagg | 60 |
| tcagcggcgc | cgtgtcgtcc | gtcaccgtgg | agaggatgct | cacggtgacg | gcgtcggtgg | 120 |
| aggcgtcgcc | ggccatcggg | cagatgtact | tccagcgcgc | cgtcgacgac | atcggcgacc | 180 |
| tcctcggcaa | gacgctgctg | ctcgagctcg | tcagctccga | gctcgacgca | aagtcgggcg | 240 |
| tggagaagac | gcgggtgacg | gcgtacgcgc | acaagacgct | gcgggagggc | cactacgagg | 300 |
| cggagttcaa | ggtgccggcg | tcgttcgggc | cggtgggcgc | ggtgctggtg | gagaacgagc | 360 |
| accacaagga | ggtcttcatc | aaggagatca | agctcgtcac | cggcggcgac | agcagcaccg | 420 |
| ccgtcacctt | cgactgcaac | tcctgggtgc | actccaagtt | cgacaacccg | gagaagcgca | 480 |
| tcttcttcac | cctcaagtca | tacctgccgt | ccgacacgcc | caaggggctg | gaggacctga | 540 |
| ggaagaagga | cctgcaggcg | ctgcgcggcg | acgggcacgg | cgagcgcaag | gtgttcgagc | 600 |
| gcgtctacga | ctacgacgtg | tacaacgacc | tgggcgaccc | ggacaagaac | ccggcccacc | 660 |
| agcggcccgt | gctgggcggc | aacaagcagt | acccataccc | gcgccgctgc | cgcaccggcc | 720 |
| gccccaggac | caagaaggac | cccgagacgg | agatgcgcga | gggccacaac | tacgtgcccc | 780 |
| gcgacgagca | gttctcggag | gtgaagcagc | tcacgttcgg | ggccaccacg | ctgcgctccg | 840 |
| gcctgcacgc | gctgctgccg | gcgctccgcc | cgctgctcat | caacaagaag | gatctgcgct | 900 |
| tcccgcactt | ccccgccatc | gacgacctct | tcagcgacgg | catcccgctg | ccggcgcaga | 960 |
| ccgggttcga | cgccttccgc | accgtcgtcc | gcgcatggt | caagctggtg | gaggacacca | 1020 |
| ccgaccacgt | cctccgcttc | gaggtgccgg | agatgataga | gagggaccgg | ttctcgtggt | 1080 |
| tcaaggacga | ggagttcgcg | aggcagacga | tcgcggggct | caacccgctg | tgcatccagc | 1140 |
| tgctgactga | gttccccatc | aagagcaagc | tggacccgga | ggtgtacggg | ccagcggagt | 1200 |
| ccgccatcac | caaggagatc | ctggagaagc | agatgaacgg | cgcgctgacc | gtggagcagg | 1260 |
| cgctggcggc | gaagcggctg | ttcatcctgg | actaccacga | cgtgttcctg | ccctacgtgc | 1320 |
| acaaggtgcg | ggagctgcag | gacgcgacgc | tctacgcctc | gcgcaccatc | ttcttcctga | 1380 |
| cggacctggg | cacgctgatg | ccgctggcca | tcgagctgac | gcggcccaag | tcgccgac | 1438 |

<210> SEQ ID NO 18
<211> LENGTH: 464
<212> TYPE: PRT
<213> ORGANISM: Zea mays

<400> SEQUENCE: 18

Ser Ala Thr Glu Glu Val Ser Gly Ala Val Ser Ser Val Thr Val Glu
1               5                   10                  15

Arg Met Leu Thr Val Thr Ala Ser Val Glu Ala Ser Pro Ala Ile Gly
            20                  25                  30

Gln Met Tyr Phe Gln Arg Ala Val Asp Asp Ile Gly Asp Leu Leu Gly
        35                  40                  45

Lys Thr Leu Leu Leu Glu Leu Val Ser Ser Glu Leu Asp Ala Lys Ser
    50                  55                  60

Gly Val Glu Lys Thr Arg Val Thr Ala Tyr Ala His Lys Thr Leu Arg
65                  70                  75                  80

-continued

```
Glu Gly His Tyr Glu Ala Glu Phe Lys Val Pro Ala Ser Phe Gly Pro
                85                  90                  95
Val Gly Ala Val Leu Val Glu Asn Glu His His Lys Glu Val Phe Ile
            100                 105                 110
Lys Glu Ile Lys Leu Val Thr Gly Gly Asp Ser Ser Thr Ala Val Thr
        115                 120                 125
Phe Asp Cys Asn Ser Trp Val His Ser Lys Phe Asp Asn Pro Glu Lys
    130                 135                 140
Arg Ile Phe Phe Thr Leu Lys Ser Tyr Leu Pro Ser Asp Thr Pro Lys
145                 150                 155                 160
Gly Leu Glu Asp Leu Arg Lys Lys Asp Leu Gln Ala Leu Arg Gly Asp
                165                 170                 175
Gly His Gly Glu Arg Lys Val Phe Glu Arg Val Tyr Asp Tyr Asp Val
            180                 185                 190
Tyr Asn Asp Leu Gly Asp Pro Asp Lys Asn Pro Ala His Gln Arg Pro
        195                 200                 205
Val Leu Gly Gly Asn Lys Gln Tyr Pro Tyr Pro Arg Arg Cys Arg Thr
    210                 215                 220
Gly Arg Pro Arg Thr Lys Lys Asp Pro Glu Thr Glu Met Arg Glu Gly
225                 230                 235                 240
His Asn Tyr Val Pro Arg Asp Glu Gln Phe Ser Glu Val Lys Gln Leu
                245                 250                 255
Thr Phe Gly Ala Thr Thr Leu Arg Ser Gly Leu His Ala Leu Leu Pro
            260                 265                 270
Ala Leu Arg Pro Leu Leu Ile Asn Lys Lys Asp Leu Arg Phe Pro His
        275                 280                 285
Phe Pro Ala Ile Asp Asp Leu Phe Ser Asp Gly Ile Pro Leu Pro Ala
    290                 295                 300
Gln Thr Gly Phe Asp Ala Phe Arg Thr Val Val Pro Arg Met Val Lys
305                 310                 315                 320
Leu Val Glu Asp Thr Thr Asp His Val Leu Arg Phe Glu Val Pro Glu
                325                 330                 335
Met Ile Glu Arg Asp Arg Phe Ser Trp Phe Lys Asp Glu Glu Phe Ala
            340                 345                 350
Arg Gln Thr Ile Ala Gly Leu Asn Pro Leu Cys Ile Gln Leu Leu Thr
        355                 360                 365
Glu Phe Pro Ile Lys Ser Lys Leu Asp Pro Glu Val Tyr Gly Pro Ala
    370                 375                 380
Glu Ser Ala Ile Thr Lys Glu Ile Leu Glu Lys Gln Met Asn Gly Ala
385                 390                 395                 400
Leu Thr Val Glu Gln Ala Leu Ala Ala Lys Arg Leu Phe Ile Leu Asp
                405                 410                 415
Tyr His Asp Val Phe Leu Pro Tyr Val His Lys Val Arg Glu Leu Gln
            420                 425                 430
Asp Ala Thr Leu Tyr Ala Ser Arg Thr Ile Phe Phe Leu Thr Asp Leu
        435                 440                 445
Gly Thr Leu Met Pro Leu Ala Ile Glu Leu Thr Arg Pro Lys Ser Pro
    450                 455                 460

<210> SEQ ID NO 19
<211> LENGTH: 50
<212> TYPE: PRT
<213> ORGANISM: CONSENSUS SEQUENCE
<220> FEATURE:
```

```
<221> NAME/KEY: UNSURE
<222> LOCATION: (2)
<223> OTHER INFORMATION: Xaa = Ser, Tyr, or Val
<221> NAME/KEY: UNSURE
<222> LOCATION: (3)
<223> OTHER INFORMATION: Xaa = ANY AMINO ACID
<221> NAME/KEY: UNSURE
<222> LOCATION: (4)
<223> OTHER INFORMATION: Xaa = Trp, Tyr, Val, or Ile
<221> NAME/KEY: UNSURE
<222> LOCATION: (6)
<223> OTHER INFORMATION: Xaa = Gln or Gly
<221> NAME/KEY: UNSURE
<222> LOCATION: (8)
<223> OTHER INFORMATION: Xaa = Ile or Val
<221> NAME/KEY: UNSURE
<222> LOCATION: (13)
<223> OTHER INFORMATION: Xaa = Asn or His
<221> NAME/KEY: UNSURE
<222> LOCATION: (18)
<223> OTHER INFORMATION: Xaa = Ile, Met, or Leu
<221> NAME/KEY: UNSURE
<222> LOCATION: (24)
<223> OTHER INFORMATION: Xaa = Ala, Ser, or Thr
<221> NAME/KEY: UNSURE
<222> LOCATION: (26)
<223> OTHER INFORMATION: Xaa = Asn or His
<221> NAME/KEY: UNSURE
<222> LOCATION: (28)
<223> OTHER INFORMATION: Xaa = Gln, His, or Arg
<221> NAME/KEY: UNSURE
<222> LOCATION: (32)
<223> OTHER INFORMATION: Xaa = ANY AMINO ACID
<221> NAME/KEY: UNSURE
<222> LOCATION: (35)
<223> OTHER INFORMATION: Xaa = Ile or Val
<221> NAME/KEY: UNSURE
<222> LOCATION: (36)
<223> OTHER INFORMATION: Xaa = His or Gln
<221> NAME/KEY: UNSURE
<222> LOCATION: (40)
<223> OTHER INFORMATION: Xaa = ANY AMINO ACID
<221> NAME/KEY: UNSURE
<222> LOCATION: (43)
<223> OTHER INFORMATION: Xaa = Tyr or Phe
<221> NAME/KEY: UNSURE
<222> LOCATION: (44)
<223> OTHER INFORMATION: Xaa = Arg or Lys
<221> NAME/KEY: UNSURE
<222> LOCATION: (47)
<223> OTHER INFORMATION: Xaa = Leu or Met
<221> NAME/KEY: UNSURE
<222> LOCATION: (48)
<223> OTHER INFORMATION: Xaa = ANY AMINO ACID

<400> SEQUENCE: 19

Asp Xaa Xaa Xaa His Xaa Leu Xaa Ser His Trp Leu Xaa Thr His Ala
 1               5                  10                  15

Val Xaa Glu Pro Phe Val Ile Xaa Thr Xaa Arg Xaa Leu Ser Val Xaa
            20                  25                  30

His Pro Xaa Xaa Lys Leu Leu Xaa Pro His Xaa Xaa Asp Thr Xaa Xaa
        35                  40                  45

Ile Asn
    50

<210> SEQ ID NO 20
<211> LENGTH: 32
<212> TYPE: PRT
<213> ORGANISM: CONSENSUS SEQUENCE
<220> FEATURE:
<221> NAME/KEY: UNSURE
<222> LOCATION: (4)
<223> OTHER INFORMATION: Xaa = Val or Ile
<221> NAME/KEY: UNSURE
```

```
<222> LOCATION: (5)
<223> OTHER INFORMATION: Xaa = Ala, Gly, or Ser
<221> NAME/KEY: UNSURE
<222> LOCATION: (2)
<223> OTHER INFORMATION: Xaa = Ser, Tyr, or Val
<221> NAME/KEY: UNSURE
<222> LOCATION: (12)
<223> OTHER INFORMATION: Xaa = Val or Leu
<221> NAME/KEY: UNSURE
<222> LOCATION: (20)
<223> OTHER INFORMATION: Xaa = Ala or Gly
<221> NAME/KEY: UNSURE
<222> LOCATION: (22)
<223> OTHER INFORMATION: Xaa = Tyr or Phe
<221> NAME/KEY: UNSURE
<222> LOCATION: (23)
<223> OTHER INFORMATION: Xaa = Leu, Ile, Val, or His
<221> NAME/KEY: UNSURE
<222> LOCATION: (24)
<223> OTHER INFORMATION: Xaa = Pro or Leu
<221> NAME/KEY: UNSURE
<222> LOCATION: (28)
<223> OTHER INFORMATION: Xaa = Thr or Ser
<221> NAME/KEY: UNSURE
<222> LOCATION: (29)
<223> OTHER INFORMATION: Xaa = ANY AMINO ACID

<400> SEQUENCE: 20

Ile Ile Trp Xaa Xaa Ser Ala Leu His Ala Ala Xaa Asn Phe Gly Gln
 1               5                  10                  15

Tyr Pro Tyr Xaa Gly Xaa Xaa Xaa Asn Arg Pro Xaa Xaa Ser Arg Arg
            20                  25                  30

<210> SEQ ID NO 21
<211> LENGTH: 8
<212> TYPE: PRT
<213> ORGANISM: CONSENSUS SEQUENCE

<400> SEQUENCE: 21

Gly Ile Pro Asn Ser Ile Ser Ile
 1               5
```